United States Patent [19]

Price et al.

[11] Patent Number: 5,767,084
[45] Date of Patent: Jun. 16, 1998

[54] METHOD OF TREATMENT FOR CYSTIC FIBROSIS AND PEPTIDES FOR SAME

[75] Inventors: Elmer M. Price, Hartsburg; Lane L. Clarke, Columbia, both of Mo.

[73] Assignee: The Curators of the University of Missouri, Columbia, Mo.

[21] Appl. No.: 539,853

[22] Filed: Oct. 6, 1995

[51] Int. Cl.[6] .......................... A61K 38/07; A61K 38/08; C07K 5/103; C07K 7/06
[52] U.S. Cl. .................... 514/16; 514/2; 514/18; 514/851; 530/300; 530/329; 530/330
[58] Field of Search .................. 530/330, 329, 530/322, 395, 324, 300, 350, 848; 514/18, 17, 16, 851, 8, 2, 12, 21

[56] References Cited

U.S. PATENT DOCUMENTS

| | | | |
|---|---|---|---|
| 4,439,196 | 3/1984 | Higuchi | 604/890 |
| 4,447,224 | 5/1984 | DeCant, Jr. et al. | 604/67 |
| 4,447,233 | 5/1984 | Mayfield | 604/152 |
| 4,475,196 | 10/1984 | La Zor | 371/29 |
| 4,486,194 | 12/1984 | Ferrara | 604/897 |
| 4,487,603 | 12/1984 | Harris | 604/152 |
| 4,959,217 | 9/1990 | Sanders et al. | 424/473 |
| 5,077,276 | 12/1991 | Ballard et al. | 514/12 |
| 5,167,616 | 12/1992 | Haak et al. | 604/20 |
| 5,169,383 | 12/1992 | Gyory et al. | 604/20 |
| 5,225,182 | 7/1993 | Sharma | 424/9 |
| 5,358,934 | 10/1994 | Borovsky et al. | 514/17 |

FOREIGN PATENT DOCUMENTS

| | | |
|---|---|---|
| 458535 | 11/1991 | European Pat. Off. . |
| 9404671 | 3/1994 | WIPO . |

OTHER PUBLICATIONS

Sato et al. Glycerol Reverses the Misfolding Phenotype. J. of Biol. Chem. 12 Jan. 1996, vol. 271, No. 2, pp. 635–638.
Jones et al. Molecular Cloning and Transcript Mapping. Mol. Gen. Genet. 1989. vol. 219, pp. 397–403.

Boat et al., "Cystic Fibrosis" In C.R. Schriver, A.L. Beudet, W S Sly, and D. Valle, Editors. *The Metabolic Basis of Inherited Disease*, 6th ed. McGraw–Hill, New York 2649–2680 (1989).

Boucher et al., "$Na^+$ Transport in Cystic Fibrosis Respiratory Epithelial: Abnormal Basal Rate and Response to Adenylate Cyclase Activation". *J. Clin. Invest.*, 78:1245–1252 (1986).

Cheng et al., "Defective Intracellular Transport and Processing of CFTR Is The Molecular Basis of Most Cystic Fibrosis" *Cell*, 63, 827–834 (1990).

Ciaccia and Price, Immumohistochemistry of Recombinant Cystic Fibrosis Transmembrane Conductance Regulator (CFTR) Expressed in Insect Cells: *IBI FLAG Epitope*, 1, 4–5 (1992).

Denning et al., "Processing of Mutant Cystic Fibrosis Transmembrane Conductance Regulator is Temperature–Sensitive" *Nature*, 358, 761–764 (1992).

Frizzell et al., "Altered Regulation of Airway Epithelial Cell Chloride Channels in Cystic Fibrosis" *Science*, 233:558–560 (1986).

(List continued on next page.)

Primary Examiner—Jeffrey E. Russel
Attorney, Agent, or Firm—Kohn & Associates

[57] ABSTRACT

Peptides derived from mutant CFTR protein which inhibit intracellular degradation and/or retention of mutant CFTR proteins are disclosed. A method of inhibiting intracellular degradation and/or retention of mutant CFTR protein by administering peptides having an amino acid sequence corresponding to mutant CFTR amino acid sequences is also disclosed. Further, a method of preventing cellular retention and degradation of an otherwise membrane bound protein by competitively inhibiting intracellular degradation (proteolysis) and retention which would otherwise retain or degrade synthesized mutant proteins prior to arrival of the protein at the cell surface is disclosed.

3 Claims, 3 Drawing Sheets

TREATMENT OF CF CELL WITH IIGV

OTHER PUBLICATIONS

Knowles et al., "Abnormal Ion Permeation Through Cystic Fibrosis Respiratory Epithelium" *Science*, 221:1067–1070 (1983).

Li et al., "The Cystic Fibrosis Mutation (ΔF508) Does Not Influence The Chloride Channel Activity of CFTR" *Nature Genetics*, 3, 311–316 (1993).

Lukacs et al., "The ΔF508 Mutation Decreases The Stability of Cystic Fibrosis Transmembrane Conductance Regulator In The Plasma Membrane" *J. Biol. Chem.*, 268, 21592–21598 (1993).

Pind et al., Participation of the Endoplasmic Reticulum Chaperone Calnexin (p88, IP90) in the Biogenesis of the Cystic Fibrosis Transmembrane . . . *J. Biol. Chem.*, 269, 12784–12788 (1994).

Quinton, "Chloride Impermeability In Cystic Fibrosis" *Nature*, 301:421–422 (1983).

Quinton, "Cystic Fibrosis: A Disease in Electrolyte Transport" *FASEB J.*, 4:2709–2717 (1990).

Riordan et al., "Identification of the Cystic Fibrosis Gene: Cloning and Characterization of Complementary DNA" *Science*, 245:1066–1073 (1989).

Sarkadi et al., "Biochemical Characterization of the Cystic Fibrosis Transmembrane Conductance Regulator in Normal and Cystic Fibrosis Epithelial Cells" *J. Biol. Chem.*, 267, 2087–2095 (1992).

Welsh and Smith, "Molecular Mechanism of CFTR Chloride Channel Dysfunction in Cystic Fibrosis" *Cell*, vol. 73, 1251–1254 (1993).

Yang et al., The Common Variant of Cystic Fibrosis Transmembrane Conductance Regulator is Recognized by hsp70 and degraded in a Pre–Golgi . . . : *Proc. Natl. Acad. Sci. USA*, 90, 9480–9484 (1993).

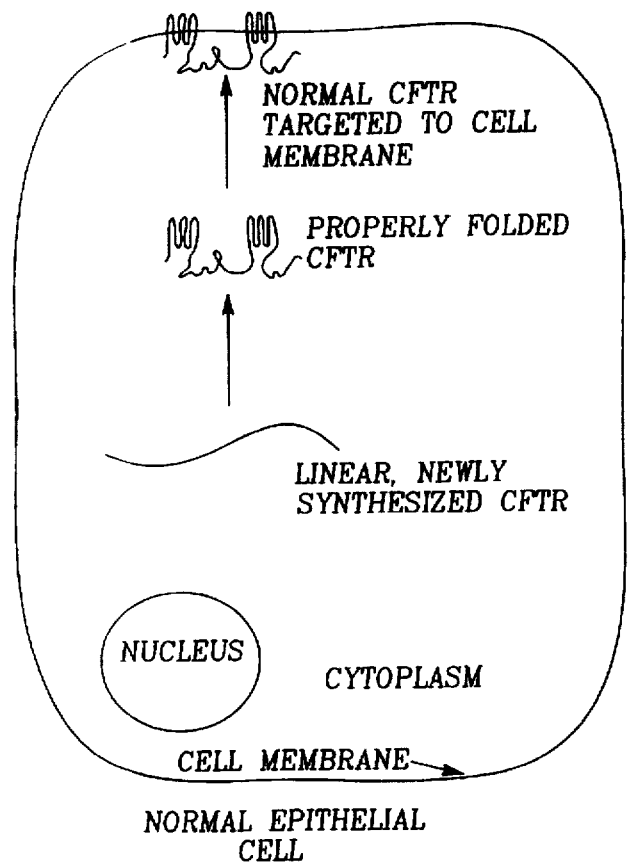
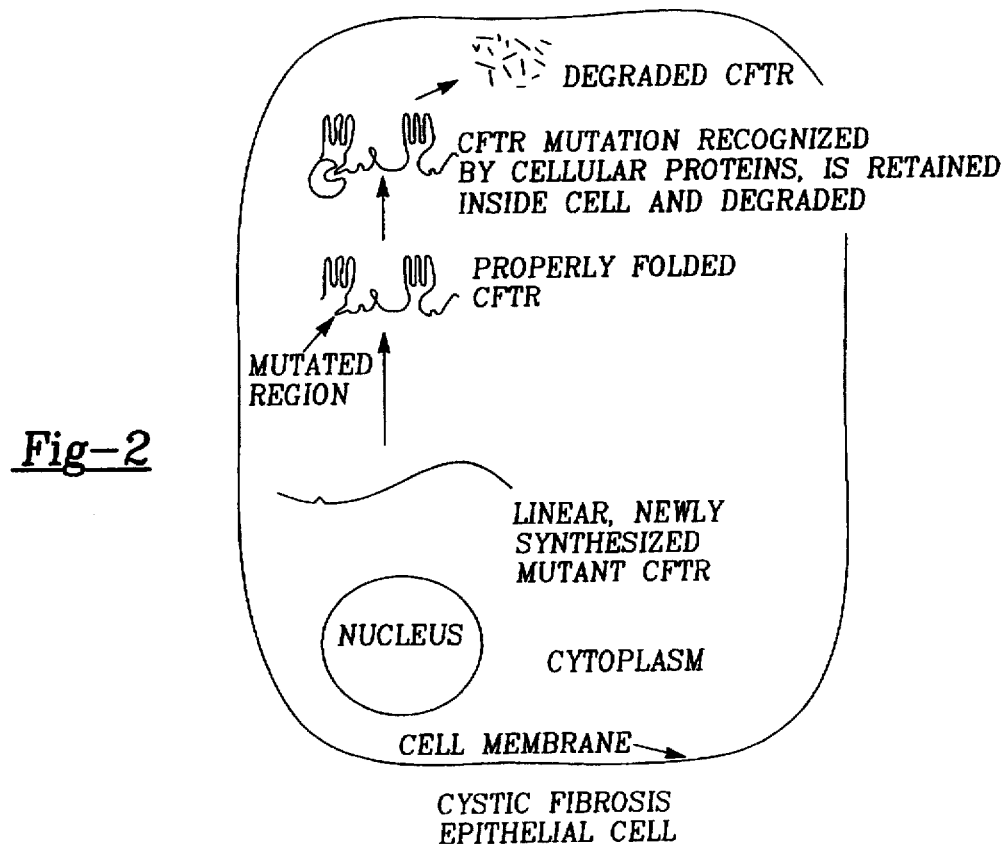
Fig-1
PRIOR ART
Fig-2

PROPOSED MECHANISM
OF MUTANT CFTR DEGRADATION

TREATMENT OF CF CELL
WITH IIGV 5,767,084

METHOD OF TREATMENT FOR CYSTIC FIBROSIS AND PEPTIDES FOR SAME

TECHNICAL FIELD

The present invention relates to a therapeutic treatment for cystic fibrosis, particularly to the amelioration of defects caused by mutations in the protein designated the Cystic Fibrosis Transmembrane Conductance Regulator (CFTR).

BACKGROUND OF THE INVENTION

Cystic Fibrosis (CF) is the most common fatal genetic disease among persons of Caucasian origin. The frequency of the disease in this population is approximately 1 in 2500 live births [Boat et al., 1989], which translates into a carrier frequency of approximately 1 in 25. CF is associated with a widespread defect in the secretory processes of all secretory epithelia. Patients with CF, who rarely live for more than 30 years, exhibit abnormalities in a variety of respiratory, gastrointestinal, and genitourinary tract systems, as well as elevated sweat electrolyte concentrations. Patients with CF exhibit abnormally viscid mucous secretions that block the airways and the pancreatic ducts. The blockage of the airways and the pancreatic ducts are responsible for the two most clinically important manifestations of CF, that being chronic pulmonary infections and pancreatic insufficiency.

More recent, studies have shown that the above manifestations are likely related to abnormal ion transport in the secretory epithelia of the affected organ [Quinton, 1983; Knowles et al., 1983; Frizzell et al., 1986; Boucher et al., 1986; Quinton, 1990]. Perhaps the most far reaching significance in this regard was the identification of reduced Cl⁻ permeability in isolated sweat ducts and nasal epithelia of patients with CF. This observation led to the conclusion that a fundamental defect in the transport of chloride (Cl⁻) ions, and possibly other anions, across epithelial cells must exist.

The relative impermeability of epithelial cell membranes to Cl⁻ ions appears to be the primary defect in CF. The molecular basis (the gene) for this defect in Cl⁻ ion transport was mapped and identified in 1989 [Riordan et al., 1989]. The protein product of the CF-associated gene is called the Cystic Fibrosis Transmembrane Conductance Regulator (CFTR). The CFTR protein is a single protein of approximately 170 kd and is made up of two repeated elements, each comprising six transmembrane segments and a nucleotide binding domain. The two repeats are separated by a large, polar, so called R domain containing multiple potential phosphorylation sites.

Normal CFTR protein in healthy individuals is found on the plasma membrane of epithelial cells, which are the cells which line the airway, gastrointestinal tract, and other ducts in the body. Mutant CFTR in nearly all CF patients is inappropriately targeted in the epithelia of CF patients, never appearing on the membrane of the cell.

The most common mutation responsible for CF disease is a deletion of a single amino acid (phenylalanine) at amino acid position 508. This mutation is designated "ΔF508". The ΔF508 mutation results in an abnormal folding or improper maturation of the CFTR protein which is thought to be responsible for the improper localization of the mutant CFTR. Normal CFTR is said to be "mature" when it has been glycosylated. Glycosylation refers to the addition of carbohydrate molecules to the protein. This is performed in the endoplasmic reticulum and Golgi apparatus inside of the cell. This glycosylation increases the molecular weight of the CFTR protein by about 30 Kd. The mutant ΔF508 CFTR is immature (not glycosylated). This means that the mutant protein is not modified by the addition of carbohydrate molecules. This, in turn, means that the mutant protein has a molecular weight which is about 30 Kd less that the mature, normal protein. It is thought that the mutation itself is responsible for the inability of the cell to process the mutant protein from an immature form to a mature form. This is thought to be due to the fact that the mutation prevents the mutant protein from moving from the endoplasmic reticulum to the golgi and, ultimately, to the cell surface.

The mutant CFTR protein ΔF508 CFTR is indeed synthesized in CF cells; however, it is retained on the inside of the cell where it appears to be rapidly degraded. Studies have shown that the mutant CFTR protein possesses similar functional characteristics to those of the normal CFTR protein, but that it simply does not reach the correct cellular location (the cell surface). [Cheng et al., 1990; Denning et al., 1992; Li et al., 1993; Yang et al., 1993].

Current therapies for the treatment of CF include physical therapy, nutritional therapy, and antibiotic therapy. These treatments are all directed toward treatment of the symptoms or effects of the disease. These therapeutic modalities target the secondary effects of the disease; namely, obstructed airways, malnutrition, and chronic bacterial infections in the lungs. None of these approaches address the primary defect of the disease, the mutant CFTR protein. Therefore, in spite of the advances in the clinical management of CF, patients with CF rarely live past thirty years of age. A therapeutic modality or agent for the treatment of CF which is targeted at remedying or curing the primary defect in CF, that being, correcting the mutant CFTR protein, would be highly desirable.

Furthermore, it would useful to have biologically active compounds, such as peptides, which can be used as drugs to prevent the intracellular degradation of mutant CFTR protein to allow the mutant CFTR protein to reach its correct cellular location and function normally, thereby providing a modality for treating Cystic Fibrosis at the level of correcting the mutant CFTR protein.

SUMMARY OF THE INVENTION AND ADVANTAGES

According to the present invention, unique, synthetic peptides derived from mutant CFTR protein having an anti-degradation and/or anti-retention effect are disclosed. These biologically active peptides can be used to inhibit intracellular degradation (proteolysis) and/or retention processes and can be used to treat or cure Cystic Fibrosis disease.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a diagrammatical illustration of a normal epithelial cell;

FIG. 2 is a diagrammatical illustration depicting a current model for the mis-targeting and degradation of mutant CFTR;

DETAILED DESCRIPTION OF THE INVENTION

Figure 3:
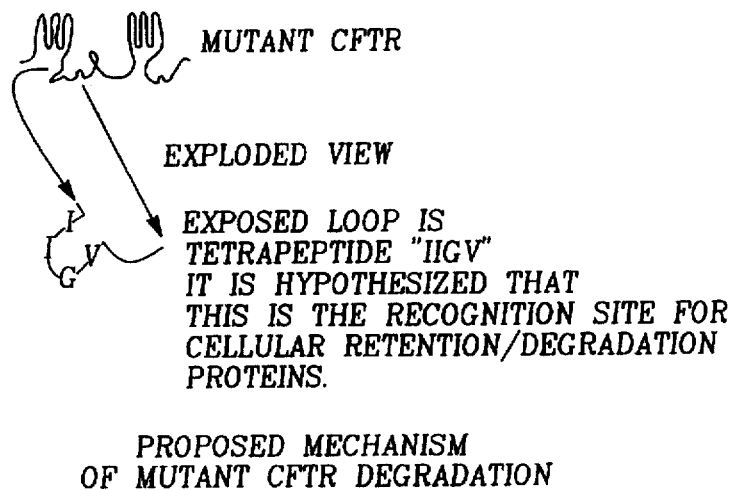
FIG. 3 is a diagrammatical illustration showing an enlarged view of the region surrounding the position of amino acid 508 on the mutant CFTR protein having amino acid sequence designated as SEQ ID No: 1.

The present invention provides isolated peptides and pharmaceutical compositions containing the peptides which inhibit degradation (proteolysis) and/or retention of mutant CFTR protein by inhibiting the action of intracellular degradation proteases and retention processes directed at the mutant CFTR protein. These biologically active peptides can be used to inhibit the action of these degradation and retention processes and thereby have utility in treating the disease Cystic Fibrosis (CF).

In a preferred embodiment, the peptide is derived from the mutated region of the CFTR protein. Specifically, the peptides of the present invention are derived from the ΔF508 CFTR protein sequence.

Other peptides can be designed based on other mutations that are known to be trafficking or processing mutations. Examples of other trafficking or processing mutations which may be corrected with synthetic peptides include:
ΔI507 (deletion of isoleucine at position 507);
S549I (serine at position 549 changed to isoleucine);
S549R (serine changed to arginine);
A559T (alanine at position 559 changed to threonine);
N1303K (asparagine at 1303 changed to lysine) and are discussed in [Welsh et al., 1993].

The ΔF508 CFTR mutation is the most common mutation responsible for CF disease and is a deletion of a single amino acid (phenylalanine) at position 508 of the CFTR protein. The synthetic peptides of the present invention correspond to the specific region of the mutant CFTR protein.

The synthetic peptides have amino acid sequences which have a high degree of similarity to the mutant CFTR protein. Portions of the amino acid sequences of the synthetic peptides can be very nearly identical or even identical to the amino acid sequence of the native mutant CFTR protein.

One such peptide includes the tetrapeptide (IIGV) Ile-Ile-Gly-Val, designated (SEQ ID No: 1). This peptide contains the exact amino acid sequence of the four amino acids (two on either side) of the region surrounding position 508 in the mutant CFTR protein. The sequence of this region in normal CFTR is designated IIFGV (Ile-Ile-Phe-Gly-Val) (SEQ ID No: 3) and the sequence of the same region in the mutant CFTR is IIGV (SEQ ID No: 1).

Another synthetic peptide embodying the present invention is designated NAc-IIGV (SEQ ID No: 1), which has the same amino acid sequence as the peptide designated IIGV (SEQ ID No: 1) but further includes an acetyl group at the amino terminus.

Yet another peptide prepared in accordance with the present invention NIIGVSY (SEQ ID No: 2), is provided and corresponds to a slightly larger region of the CFTR protein surrounding the phenylalanine 508 position in the CFTR protein. These peptides are provided as examples of synthetic peptides having amino acid sequences corresponding to the ΔF508 CFTR mutant protein but, are not meant to provide an exhaustive list of all of the possible derivatives or analogs of the ΔF508 CFTR mutant protein (or normal CFTR protein) which can be used to accomplish the present invention.

Significant features of the peptide compounds of the present invention include their hydrophobicity; the nature of the side-chains of the four amino acids of IIGV (SEQ ID No: 1), and their similarity to the mutated region of the CFTR protein. It is also hypothesized that the two hydrophobic residues (I; isoleucine) followed by a glycine (G, which, having no side chain, imparts a specific structure such as a bend or kink to the synthetic peptide) followed by another hydrophobic amino acid such as (V; valine). These biophysical properties of IIGV (SEQ ID No: 1) may be determinants of the efficacy of these compounds. The small size and hydrophobicity of IIGV (SEQ ID No: 1) (and related peptides) are thought to aid in the bioavailability of the peptide. These features allow the peptide to be easily adsorbed by the tissues of an animal (including man) and then readily enter the cell via simple diffusion. The properties of IIGV (SEQ ID No: 1) also appear to render the peptide itself resistant to proteolysis, which would lend to the stability of the peptide once administered to an animal (including man). Larger peptides might be more prone to such degradation. However, it may be possible that small peptides corresponding to this region from the normal protein may be useful. This would correspond to the peptide IIFGV (SEQ ID No: 3).

The synthetic peptides of the present invention are constructed based on the ΔF508 CFTR protein and are selected such that the sequence of the synthetic peptide function biologically to prevent the intracellular degradation and/or retention of mutant CFTR protein so that the mutant CFTR protein is able to be targeted or proceed to its functional location on the membrane surface of the cell.

The ΔF508 mutation prevents the CFTR protein from reaching its functional location at the cell's surface. Data exists [Cheng et al., 1990; Yang et al., 1993; Lukacs et al., 1993] which suggests that ΔF508 CFTR does not exit the endoplasmic reticulum and that it is degraded more rapidly than is the wildtype CFTR. It is thought that specific retention proteins and degradation proteases are capable of recognizing the mutant CFTR protein and that these retention/degradation proteins are somehow involved in the processing defect associated with the mutation. It is proposed that the mutation (ΔF508) exposes a region of the CFTR which is recognized by the retention/degradation factors. This region, which is postulated to include the sequence IIGV (SEQ ID No: 1), is buried and inaccessible in normal CFTR. Once bound by these factors the mutant protein is prevented from maturing and is degraded.

It is further proposed that these retention and degradation proteins interact with the ΔF508 CFTR protein and bind to specific regions of the CFTR protein and cause either degradation and/or mistargeting of the mutant protein which prevent the mutant protein from reaching its location on the cell surface.

Referring to FIG. 1, a normal epithelial cell is shown. The cell membrane is a lipid bilayer which surrounds the cell and is the location where the normal CFTR protein resides. This Figure depicts newly synthesized CFTR as a linear molecule, which is then folded into a 3-dimensional, globular structure. The properly folded protein is then translocated and inserted into the cell membrane. This process is referred to as "targeting."

FIG. 2 illustrates the proposed mechanism of mistargeting of mutant CFTR. Newly synthesized CFTR, in Cystic Fibrosis, is shown as the mutated form missing the amino acid at position 508. This mutation is thought to disturb the structure of the CFTR, shown as a bump in the newly synthesized CFTR molecule. The mutant CFTR is then folded into its abnormal 3-dimensional structure, which is a structure different from that assumed by the normal protein. The region of the 3-dimensional structure of the mutant protein which is caused by the ΔF508 deletion is shown as a bump in the folded CFTR protein and is labeled in FIG. 2 as the "mutated region". It is proposed that this abnormal structure is recognized by the intracellular retention and degradation proteins (shown in the Figure as a small circle with a "mouth") which are responsible for the retention and/or degradation of the mutant CFTR protein inside the cell.

FIG. 3 is an enlarged view of the region of the mutant CFTR protein surrounding the position of amino acid 508. It is hypothesized that this region, in the normal protein, is buried inside the 3-dimensional structure of the protein.

It is further hypothesized that in the mutant protein, the sequence IIGV (SEQ ID No: 1) (which are the amino acids which surround the position 508, which is the exact region mutated in Cystic Fibrosis) is now exposed or unburied and bulges out of the CFTR protein. This unburied and bulging sequence is recognized by the intracellular proteins responsible for the retention and/or degradation of the mutant CFTR protein.

At this time, these retention/degradation factors have not yet been thoroughly characterized. However, preliminary data suggests that the proteins Hsp 70 [Yang et al., 1993] and calnexin [Pind et al., 1994] may somehow be involved.

Figure 4:
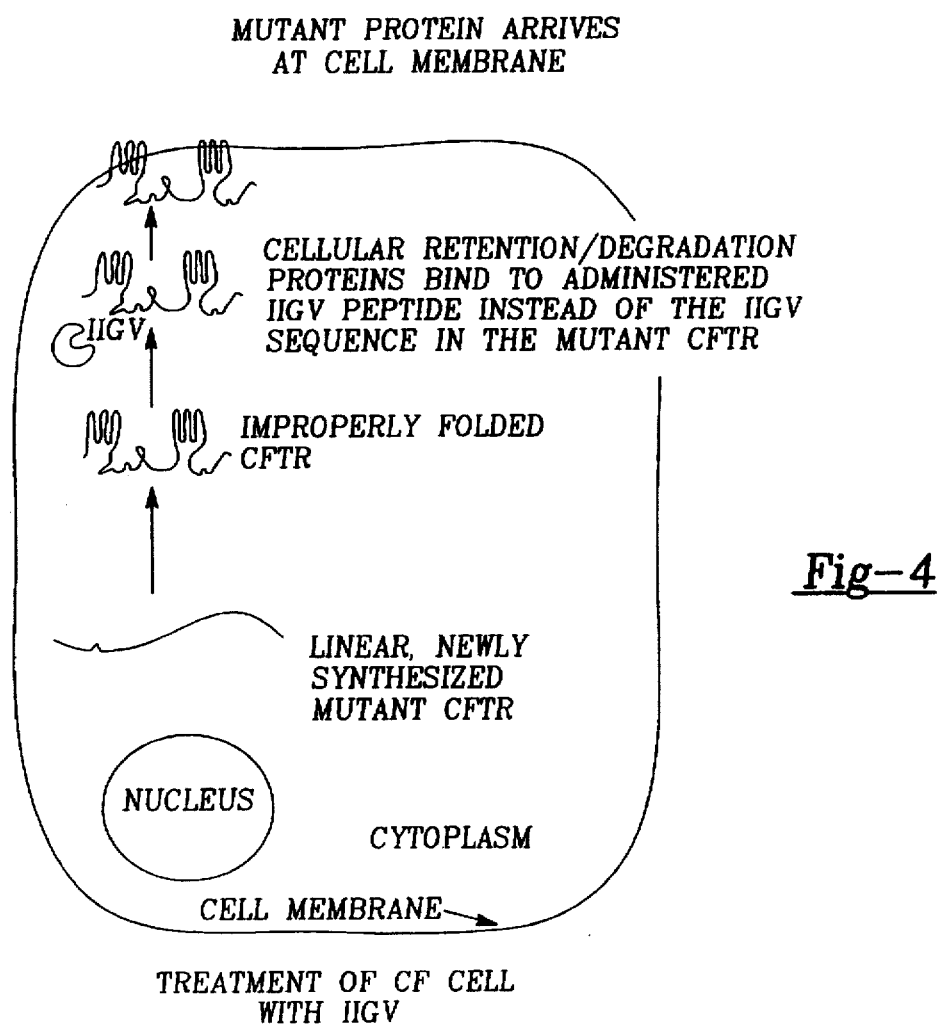
FIG. 4 is a diagrammatical illustration showing the proposed mechanism of operation of the peptides of the present invention having amino acid sequence designated as SEQ ID No: 1 on an epithelial cell expressing the mutant CFTR.

The synthetic peptides of the present invention are administered to inhibit or prevent the degradation of the mutant CFTR protein within the epithelial cell. Referring specifically to FIG. 4, a diagrammatical illustration of the proposed mechanism for the prevention of degradation or the inhibition of the degradation or retention proteins is provided. A CF epithelial cell is treated with IIGV (SEQ ID No: 1), the synthetic peptide described above which corresponds to the region within the mutant CFTR sequence which is hypothesized to interact with the intracellular retention and/or degradation proteins. Although this sequence is in the CFTR protein, if an excess of "free", exogenous IIGV (SEQ ID No: 1) is provided to the cell, the retention and/or degradation proteins which would have normally bound to the mutant CFTR protein, now bind to the extra molecules of IIGV (SEQ ID No: 1) synthetic peptide. That is, an excess of exogenous IIGV (SEQ ID No: 1) is provided to the CF cell such that the synthetic peptides competitively inhibits or saturates the binding sites on the retention and/or degradation proteins which would have bound to the mutant CFTR protein. By binding to the sites on the retention and/or degradation proteins which would have bound to the mutant CFTR protein causing its degradation and preventing its targeting to the cell membrane, the synthetic peptides inhibit or prevent the retention and/or degradation proteins from acting on the mutant CFTR protein, thereby allowing the mutant CFTR protein to be properly targeted and function properly.

FIG. 4 illustrates the mechanism of action of the synthetic peptides of the present invention. This proposed mechanism of action involves administering an excess amount of exogenous IIGV (SEQ ID No: 1) synthetic peptide to competitively bind or saturate the mutant CFTR binding sites located on the retention and/or degradation proteins to prevent these compounds or proteins from retaining or degrading the mutant CFTR protein. By preventing the retention or degradation of the mutant CFTR protein, the protein is allowed to be targeted properly and locate on the cell surface where it functions normally.

The peptides of the present invention are synthetic peptides based on the sequence of the mutant CFTR protein Unlike other compounds which are used as drugs, a synthetic peptide is safer, since its metabolites are simply amino acids.

The peptides were synthesized using an Applied Biosystems 431A peptide synthesizer using f-moc chemistries as is well known in the art.

The peptides of the present invention are administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art. The amount must be effective to prevent a substantial amount of degradation of the mutant CFTR protein. There are at least three different clinical parameters which can be used to measure the success of CF treatment using these peptides. CF patients, after taking the peptide for a specified length of time, can be subject to a sweat electrolyte test. This is the same clinical test which is used to diagnose CF, and if the peptide is successful at correcting the primary defect of the mutant protein, then the sweat electrolyte values should return to normal. A second test would be the assessment of the nasal PD (potential difference), which is an electrophysiological assay of the ion transport across the nasal epithelium. This is elevated in CF and correction via peptide therapy should return the values to normal. A third clinical parameter would be the FEV (forced exhalation volume), which is a direct measurement of lung capacity. This is an important clinical parameter which steadily declines over time in CF disease. Successful treatment should prevent a worsening of the FEV in CF patients.

In the method of the present invention, the peptide can be administered in various ways. It should be noted that the peptide can be administered as the compound or as pharmaceutically acceptable salt and can be administered alone or in combination with pharmaceutically acceptable carriers designed to maintain the integrity of the compound. Protection of the peptides may not be necessary to protect the peptides against degradation as it is predicted that the peptides are resistant to proteolysis. The compounds can be administered orally, subcutaneously, topically or parenterally including intravenous, intraarterial, intramuscular, intraperitoneally, inhalant (similar to how asthmatics receive drugs) and intranasal administration. Implants of the compounds are also useful. The patient being treated is a warm-blooded animal and, in particular, mammals including man. The doses may be single doses or multiple doses over a prolonged period. The treatment generally has a length proportional to the length of the disease process and drug effectiveness and the patient species being treated.

When administering the peptide parenterally, the peptide will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such as cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the peptide can be administered to the patient in an injectable formulation containing any compatible carrier, such as various vehicle, adjuvants, additives, diluents and antiproteolytic agents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. No. 5,225,182; U.S. Pat. No. 5,169,383; U.S. Pat. No. 5,167,616; U.S. Pat. No. 4,959,217; U.S. Pat. No. 4,487,603; U.S. Pat. No. 4,486,194; U.S. Pat. No. 4,447,233; U.S. Pat. No. 4,447,224; U.S. Pat. No. 4,439,196; and U.S. Pat. No. 4,475,196. Many other such implants, delivery systems, and modules are well known to those skilled in the art.

A pharmacological formulation of the peptide utilized in the present invention can be administered orally to the patient. Conventional methods such as administering the compounds in tablets, suspensions, solutions, emulsions, capsules, powders, syrups and the like are usable. Known techniques which deliver the peptide orally or intravenously and retain the biological activity are preferred.

A pharmaceutical formulation of the period utilized in the present invention can be inhaled by the patient in the form of an aerosol.

An analog will be generally at least 70% homologous over any portion that is functionally relevant. In more preferred embodiments the homology will be at least 80% and can approach 95% homology to the ΔF508 CFTR protein. The homology will extend over a region of at least four contiguous amino acids. The amino acid sequence of an analog may differ from that of the ΔF508 CFTR protein when at least one residue is deleted, inserted or substituted. Analogs of the peptide may be those where specific amino acids are replaced with homologous amino acids. An example, is ILGV, designated (SEQ ID No: 4), an analog of IIGV (SEQ ID No: 1), where the second isoleucine is replaced with a leucine.

Additionally, derivatives of the peptides, such as by acetylating or otherwise treating or modifying the protein to achieve desired properties can also be performed in the present invention. Specific modifications can be performed which modify, for example, the hydrophobicity of the peptides in order to enhance their efficacy. This can entail modifying the amino-terminus of the peptide with methyl, ethyl, propyl or other such groups.

The application of the synthetic peptide, such as IIGV (SEQ ID No: 1) (or related peptides), can be used to treat patients who have Cystic Fibrosis. For example, if provided as an inhalant, IIGV (SEQ ID No: 1) (or related peptides) can be used for correcting the lung disease exhibited by these individuals which is a major cause of death in this disease. Orally active variants of the peptides of the present invention may be given to ameliorate systemic aspects of Cystic Fibrosis disease including lung disease and gastrointestinal problems. Furthermore, patients who are either homozygous for the ΔF508 mutation (ΔF508/ΔF508) or compound heterozygous for ΔF508 mutation (ΔF508/other mutation) will benefit from this potential therapeutic approach.

For those diseases that result in obstructions of the airways, gastrointestinal tract, or other ducts and glands, the synthetic peptides of the present invention, such as IIGV (SEQ ID No: 1), may also be therapeutic due to its potential to increase fluid and buffer secretion. Also, IIGV (SEQ ID No: 1) may be useful in ulcer treatment since CFTR has been shown to mediate bicarbonate secretion. It is also likely that IIGV (SEQ ID No: 1) can increase the expression of normal CFTR, thereby increasing bicarbonate secretion and, therefore, reducing the acidity of gastric secretions.

As short, hydrophobic molecules, the peptides are likely entering the cell via simple diffusion. As such, no specific uptake mechanism is needed. Doses of peptide will be chosen such that the intracellular space will contain sufficient quantities of peptide such that the retention/degradation factors will be saturated. Therefore, targeting to a specific intracellular location may not be required since the cell will be saturated with an appropriate dose of peptide. While the peptide may enter all of the tissues in a treated patient, it should have no effect on a non-CFTR expressing cell.

It is proposed that no mechanism for preventing peptide degradation is needed. This is due to the fact that the peptides should be inherently resistant to proteolysis. Also, the peptides themselves are predicted to be protease inhibitors.

The peptides of the present invention also have diagnostic utility in the identification of the retention/degradation factors.

The above discussion provides a factual basis for the use of peptides derived from a specific region corresponding to the sequence of the ΔF508 CFTR protein. The methods used with and the utility of the present invention can be shown by the following examples.

EXAMPLES

General Methods

Synthetic peptides were prepared using an Applied Biosystems 431A peptide synthesizer. The peptides were dissolved in distilled water and sterilized via filtration.

Cultured cells used in these experiments were murine fibroblasts ("3T3" cells) which express the recombinant human ΔF508 CFTR mutant protein. These cells are grown at 37° C. in DMEM (Dulbecco's Modified Eagles Medium) media supplemented with 10% calf serum and antibiotics. The immunoblots shown in FIG. 5 were generated as follows: Cells in a T25 flask expressing ΔF508 CFTR, either untreated or treated with a specific peptide for a certain length of time, were lysed in standard RIPA lysis buffer well known in the art. Insoluble material was removed via centrifugation and the mutant CFTR was immunoprecipitated from the RIPA extract using a monoclonal antibody directed against an engineered epitope located in the carboxy-terminus of the CFTR protein [Ciaccia and Price, 1992]. The immunoprecipitate was electrophoresed on a 7% SDS-PAGE gel and transferred to PVDF (polyvinyl divinyl fluoride) membrane for protein immunoblot analysis. The blot was probed with an anti-CFTR polyclonal antibody as described [Sarkadi et al., 1992] and the CFTR signal was visualized via enhanced chemiluminescence. Immature, unglycosylated CFTR is seen as a protein with a molecular weight of about 140 Kd ("Band A") and mature, glycosylated CFTR is seen at a molecular weight of about 180 Kd ("Band C"). (See FIGS. 5A–D).

Figure 5A:
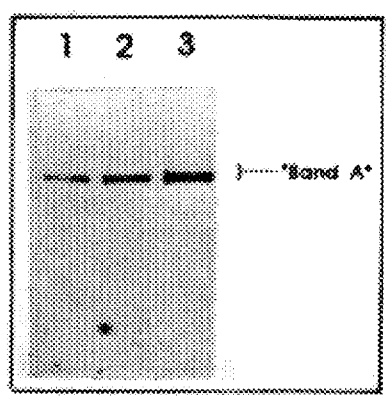
FIGS. 5A–D, Panels (A) and (B) depict luminograms from immunoblot analysis of ΔF508 CFTR expressed in cultured cells treated with increasing concentrations of IIGV (SEQ ID No: 1) wherein "Band A" identifies unprocessed immature (unglycosylated) ΔF508 CFTR, "Band C" identifies processed mature (glycosylated) ΔF508 CFTR, Panel A is from a ten minute exposure and Panel B is from an overnight exposure, Lane 1: untreated cells, Lane 2: cells treated for three days with 10 µg/ml IIGV (SEQ ID No: 1), and Lane 3: cells treated with 50 µg/ml IIGV (SEQ ID No: 1), Panels (C) and (D) are additional experiments, similar to that shown in Panels A and B, Panel C is from a sixty minute exposure and Panel D is from an overnight exposure, Lane 1: untreated cells, Lane 2: cells treated with N-acetyl-IIGV (SEQ ID No: 1) for three days (10 µg/ml), Lane 3: cells treated with 20 µg/ml N-acetyl-IIGV (SEQ ID No: 1), Lane 4: cells treated with 50 µg/ml N-acetyl-IIGV (SEQ ID No: 1), Lane 5: cells treated with 10 µg/ml IIGV (SEQ ID No: 1), Lane 6: cells treated with 20 µg/ml IIGV, and Lane 7: cells treated with 50 µg/ml IIGV (SEQ ID No: 1).
Figure 5B:
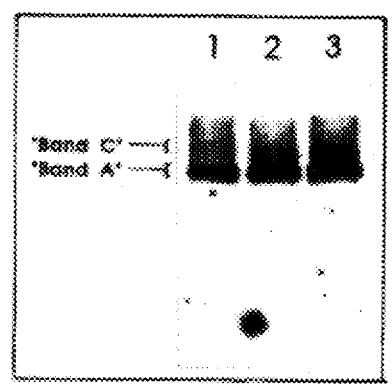

Cultured cells expressing ΔF508 CFTR were grown in the presence of different concentrations of IIGV (SEQ ID No: 1). Referring to FIGS. 5A and B, luminograms from immunoblot analysis of ΔF508 CFTR expressed in cultured cells and treated with increasing concentrations of IIGV (SEQ ID No: 1) are shown following immuno-precipitation from cultured cells. The samples were analyzed via protein immunoblots probed with a polyclonal antibody as described by Sarkadi et al., 1992. specific for CFTR. "Band A" identifies unprocessed (immature, unglycosylated) ΔF508 CFTR and "Band C" identifies processed (mature, glycosylated) ΔF508 CFTR protein. These are from the same immunoblot analyzed by a mini gel. The data shows that cells treated with IIGV (SEQ ID No: 1) had increased relative amounts of both unprocessed ("Band A") as well as properly processed ("Band C") ΔF508 CFTR protein in a dose-dependent manner.

Figure 5C:
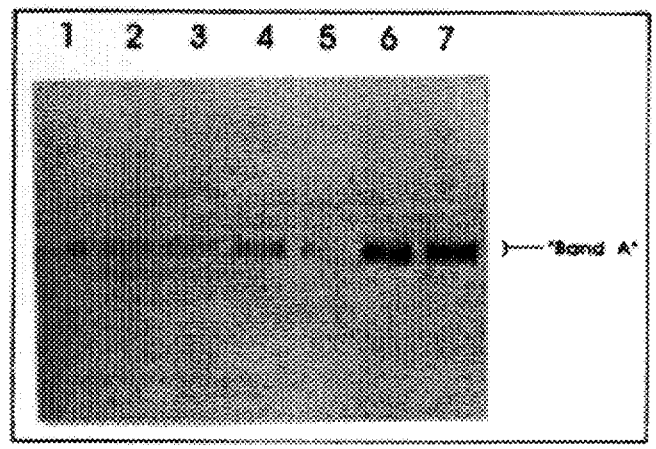
Figure 5D:
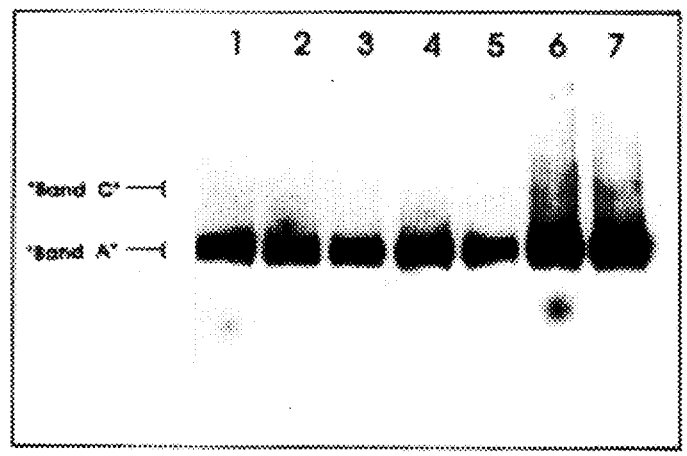

Referring to FIGS. 5C and D, the immunoblots show that IIGV (SEQ ID No: 1) (but not the related peptide N-acetyl-IIGV (SEQ ID No: 1)) increased the relative amounts of both unprocessed ("Band A") as well as properly processed ("Band C") ΔF508 CFTR protein in a dose-dependent manner. The fact that, N-acetyl-IIGV (SEQ ID No: 1) had less effect under these conditions indicates the mechanism of action of IIGV (SEQ ID No: 1) is specific.

The results indicate that IIGV (SEQ ID No: 1) not only enabled the cells to express more of the ΔF508 CFTR protein, but that it generated a higher molecular weight species of CFTR which is consistent with post-translational modification (glycosylation) and cell membrane localization. In other words, the synthetic peptides of the present invention not only enabled the cells to express more of the ΔF508 CFTR protein, but the peptides prevented the retention and/or degradation of the ΔF508 CFTR protein within the cell and allowed the ΔF508 CFTR protein to be properly targeted to the cell membrane where it can function normally. This confirms the reproducibility of the effect of IIGV (SEQ ID No: 1) and also shows the effect of a different peptide, N-acetyl-IIGV (SEQ ID No: 1). The results of the experiments shown in FIGS. 5A–D illustrate that IIGV (SEQ ID No: 1) not only prevents the degradation of the ΔF508 CFTR (witnessed by the increase in the amount of CFTR protein), but also facilitates the generation of mature protein.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood that the terminology used is intended to be in the nature of description rather than of limitation. Obviously, many modifications and variations of the present invention are possible in light of the above teachings. Therefore, it is to be understood that within the scope of the appended claims, the invention may be practiced otherwise than as specifically described.

REFERENCES CITED

Boat et al., "Cystic Fibrosis" In C. R. Scriver, A. L. Beaudet, W. S. Sly, and D. Valle. Editors. *The Metabolic Basis of Inherited Disease*. 6th ed. McGraw-Hill, New York. 2649–2680 (1989).

Boucher et al., "$Na^+$ transport in cystic fibrosis respiratory epithelial: abnormal basal rate and response to adenylate cyclase activation". *J. Clin. Invest.* 78:1245–1252 (1986).

Cheng et al., "Defective Intracellular Transport and Processing of CFTR is the Molecular Basis of Most Cystic Fibrosis" *Cell* 63, 827–834 (1990).

Ciaccia, A. V. and Price, E. M. "Immunohistochemistry of Recombinant CFTR Expressed in Insect Cells: FLAG Technology and Immunofluorescence" *IBI FLAG Epitope* 1, 4–5 (1992).

Denning et al., "Processing of Mutant Cystic Fibrosis Transmembrane Conductance Regulator is Temperature-Sensitive" *Nature* 358, 761–764 (1992).

Frizzell et al "Altered regulation of airway epithelial cell chloride channels in cystic fibrosis" *Science* 233:558–560 (1986).

Knowles et al. "Abnormal ion permeation through cystic fibrosis respiratory epithelium" *Science* 221:1067–1070 (1983).

Li et al., "The Cystic Fibrosis Mutation (ΔF508) Does Not Influence the Chloride Channel Activity of CFTR" *Nature Genetics* 3, 311–316 (1993).

Lukacs et al., "The ΔF508 Mutation Decreases the Stability of Cystic Fibrosis Transmembrane Conductance Regulator in the Plasma Membrane. Determination of Functional Half-Lives on Transfected Cells" *J. Biol. Chem* 268, 21592–21598 (1993).

Pind et al, "Participation of the Endoplasmic Reticulum Chaperone Calnexin in the Biogenesis of the Cystic Fibrosis Transmembrane Conductance Regulator" *J. Biol. Chem.* 269, 12784–12788 (1994).

Quinton, "Chloride impermeability in cystic fibrosis" *Nature* 301:421–422 (1983).

Quinton, "Cystic fibrosis: a disease in electrolyte transport" *FASEB J.* 4:2709–2717 (1990).

Riordan et al., "Identification of the cystic fibrosis gene: cloning and characterization of complementary DNA" *Science* 245:1066–1073 (1989).

Sarkadi et al., "Biochemical Characterization of the Cystic Fibrosis Transmembrane Conductance Regulator in Normal and CF Epithelial Cells" *J. Biol. Chem.* 267, 2087–2095 (1992).

Welsh and Smith, "Molecular Mechanisms of CFTR Chloride Channel Dysfunction in Cystic Fibrosis" *Cell*, Vol. 73, 1251–1254 (1993).

Yang et al., "The Common Variant of Cystic Fibrosis Transmembrane Conductance Regulator is Recognized by Hsp and Degraded in a Pre-Golgi nonlysosomal Compartment: *Proc. Natl. Acad Sci. USA*, 90, 9480–9484 (1983

We claim:

1. A method of inhibiting degradation and/or retention of mutant CFTR protein by administering a peptide consisting of the amino acid sequence Asn-Ile-Ile-Gly-Val-Ser-Tyr (SEQ ID No: 2), optionally acetylated at its amino terminus.

2. A method of preventing cellular retention and degradation of otherwise membrane bound mutant CFTR proteins by competitively inhibiting degradation and retention which would otherwise retain or degrade newly synthesized mutant CFTR proteins prior to arrival of the mutant CFTR proteins at the cell membrane by administering a peptide consisting of the amino acid sequence Asn-Ile-Ile-Gly-Val-Ser-Tyr (SEQ ID No: 2), optionally acetylated at its amino terminus.

3. A peptide consisting of the amino acid sequence Asn-Ile-Ile-Gly-Val-Ser-Tyr (SEQ ID No: 2), optionally acetylated at its amino terminus.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:1:

Ile   Ile   Gly   Val
1

( 2 ) INFORMATION FOR SEQ ID NO:2:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( x i ) SEQUENCE DESCRIPTION: SEQ ID NO:2:

Asn   Ile   Ile   Gly   Val   Ser   Tyr
1                         5

( 2 ) INFORMATION FOR SEQ ID NO:3:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( x i ) SEQUENCE DESCRIPTION: SEQ ID NO:3:

Ile   Ile   Phe   Gly   Val
1                         5

( 2 ) INFORMATION FOR SEQ ID NO:4:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:4:

Ile   Leu   Gly   Val
1